United States Patent [19]

Gibboni et al.

[11] Patent Number: 5,556,743
[45] Date of Patent: Sep. 17, 1996

[54] METHOD FOR IMMOBILIZING DYE ON SUBSTRATES

[75] Inventors: David J. Gibboni, Drexel Hill, Pa.; Wai T. Law, Sewell, N.J.

[73] Assignee: ActiMed Laboratories, Inc., Burlington, N.J.

[21] Appl. No.: 243,876

[22] Filed: May 17, 1994

Related U.S. Application Data

[63] Continuation-in-part of Ser. No. 833,423, Feb. 10, 1992, abandoned.

[51] Int. Cl.$^6$ ............... C12Q 1/00; C12Q 1/28; C12Q 1/60; G01N 33/551
[52] U.S. Cl. ............... 435/4; 435/7.92; 435/10; 435/11; 435/19; 435/25; 435/28; 435/805; 436/13; 436/63; 436/524; 436/527; 436/529; 436/530
[58] Field of Search ............... 435/4, 7.92, 18, 435/28, 805, 10, 11, 19, 25; 436/63, 800, 524, 13, 527, 529, 530

[56] References Cited

U.S. PATENT DOCUMENTS

| | | | |
|---|---|---|---|
| 3,443,939 | 5/1969 | Bloom et al. | 430/242 |
| 3,770,381 | 11/1973 | Schmitt et al. | 435/4 |
| 3,983,005 | 9/1976 | Goodhue et al. | 435/11 |
| 4,035,146 | 7/1977 | Brenner et al. | 435/4 |
| 4,038,031 | 7/1977 | Lam | 435/4 |
| 4,069,016 | 1/1978 | Wu | 435/4 |
| 4,144,306 | 3/1979 | Figueras | 435/22 |
| 4,247,297 | 1/1981 | Berti et al. | 435/4 |
| 4,247,642 | 1/1981 | Hirohara et al. | 435/180 |
| 4,251,629 | 2/1981 | Yamanisi et al. | 435/28 |
| 4,312,834 | 1/1982 | Vogel et al. | 435/4 |
| 4,312,944 | 1/1932 | Mattiasson et al. | 435/7.92 |
| 4,394,444 | 7/1983 | Cameron et al. | 435/11 |
| 4,435,504 | 3/1984 | Zuk et al. | 435/7.92 |
| 4,533,629 | 8/1985 | Litman et al. | 435/7.91 |
| 4,548,905 | 10/1985 | Wu | 435/4 |
| 4,842,976 | 6/1989 | Sanders et al. | 430/333 |
| 4,889,636 | 12/1989 | Perry et al. | 210/651 |
| 4,971,918 | 11/1990 | Bouse et al. | 436/166 |
| 4,999,287 | 3/1991 | Allen et al. | 435/11 |
| 5,087,556 | 2/1992 | Ertinghausen | 435/7.92 |

FOREIGN PATENT DOCUMENTS

| | | |
|---|---|---|
| 0029104 | 9/1980 | European Pat. Off. . |
| 0134025 | 8/1984 | European Pat. Off. . |
| 0342447 | 5/1989 | European Pat. Off. . |
| 0345460 | 12/1989 | European Pat. Off. . |
| 0415679 | 8/1990 | European Pat. Off. . |
| 1571242 | 6/1968 | France . |

OTHER PUBLICATIONS

Trinder. *Ann. Clin. Biochem.* 6:24–27, 1969.
Seitz et al. *Analytical Chemistry* vol. 61, No. 3: 202–205, Feb. 1989.
Zhujan et al, Poly(vinyl alcohol) as a Substrate for Indicator Immobilization for Fiber–Optic Chemical Sensors, Anal. Chem. 61, 202–205, 1989.

*Primary Examiner*—John Kight
*Assistant Examiner*—Louise N. Leary
*Attorney, Agent, or Firm*—Iver P. Cooper; Anne M. Kornbau

[57] ABSTRACT

A dye is covalently bound to a polymeric film, especially a polyhydric polymer, for assays and other purposes. The dye may be one which, when it comes into contact with hydrogen peroxide, changes color to indicate the presence of hydrogen peroxide. This dyed film may be used in qualitative or quantitative assays. This method chemically immobilizes dyes on support matrices with much higher yields of immobilized dye than has heretofore been possible. The covalently immobilized dye may be immobilized on solid matrix particles and combined with a free-flowing dye component to form a two component dye system. By combining a dyed film-former with a film-opener, the amount of dye available for assay is greatly enhanced. This provides a dye system which can be used to detect and measure quantitatively, accurately and precisely high levels of hydrogen peroxide. These high levels of hydrogen peroxide may result from the enzyme-mediated decomposition of various analytes from undiluted whole blood samples.

18 Claims, No Drawings

METHOD FOR IMMOBILIZING DYE ON SUBSTRATES

This application is a continuation in part of application Ser. No. 07/833,423, filed Feb. 10, 1992 now abandoned, the entire contents of which are hereby incorporated by reference.

BACKGROUND OF THE INVENTION

1. Field of the Invention

The present invention relates to methods of immobilizing dyes onto solid supports and films made thereby.

2. Description of the Background Art

The detection of component materials of fluids by means of test strips is of ever-increasing importance. In many cases, test strips provide a simple, economical and rapid detection means. Test strips are widely used in diagnosing urine qualitatively and semiquantitatively. Other test strips are used for detecting components in blood and serum in medical diagnosis. Furthermore, test strips are widely used for monitoring of beverages, drinking water, waste water and other fluids of industrial importance.

Of particular interest is cholesterol monitoring. Ideally, a patient checks his cholesterol daily or weekly to determine if the medication or diet should be adjusted to maintain the serum cholesterol levels within acceptable limits. However, there are no currently available assay devices which make it both simple and reliable for a lay person to monitor serum cholesterol levels.

A great number of clinical assays are currently in use which depend on enzyme-mediated decomposition of various analytes from undiluted whole blood samples. These assays are particularly convenient because they can be effected in a very short time, and, if a color could be developed with the high quantity of hydrogen peroxide released from the decomposition of the analyte, they would be greatly in demand for home and physicians' office use. Unfortunately, none of the prior art processes provides a matrix to which is bound or impregnated a dye in quantities sufficient to detect and measure quantitatively, accurately and precisely high levels of hydrogen peroxide that result from enzyme-mediated decomposition of various analytes from undiluted whole blood sample.

Peroxidase, because of it high turnover rate, good stability, ease of assay, and relatively low molecular weight has become widely used as a marker in enzyme immunoassays. There have been attempts to develop a sensitive and nonhazardous chromogenic reagent for this enzyme.

Peroxidase activity is generally monitored by the formation of a colored compound from a colorless oxygen acceptor according to the following equation:

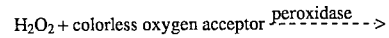

$$2H_2O + \text{colored oxidized product}.$$

Benzidine, o-tolidine, o-toluidine and o-dianisidine were commonly used oxygen acceptors. However, these compounds were shown to be carcinogenic, so that there have since been attempts to find alternative chromogens which are less hazardous.

A wide range of substrates has been described for the nonspecific peroxidase catalyzed oxidation reaction, cf., for example, U.S. Pat. Nos. 3,983,005; 4,251,629; 4,247,297; and 3,770,381. The different indicator reaction can be divided into two basic categories: (a) single chromogen, and (b) oxidative coupling of two chromogens. Commonly used chromogens such as o-dianisidine, o-tolidine, benzidine, tetramethylbenzidine (TMB) and 4-Cl-naphthol are used in dry chemistry dip stick formats, but these generally suffer from insensitivity or unstable color products.

Trinder demonstrated in 1969, in *Ann. Clin. Biochem.*. 6: 24–27, 1969, that the oxidative coupling of two chromogens in the presence of peroxidase gave intense colors that are relatively stable. Thus, chromogen systems such as phenol plus 4- aminoantipyrine, and N,N-dimethylaniline plus 3-methyl-2-benzothiazolinone hydrazone (MBTH) are commonly used.

A particularly convenient dry strip indicator for use in analyses in which hydrogen peroxide is generated is disclosed in Ertinghausen, U.S. Pat. No. 5,087,556, filed May 17, 1989 and U.S. Ser. No. 07/749,521, filed Aug. 26, 1991 now U.S. Pat. No. 5,234,813, which applications are hereby incorporated by reference in their entirety. In this type of strip, hydrogen peroxide is generated from the substrate by the catalytic reaction with oxidase, and the migrating sample front carrying the hydrogen peroxide oxidizes the immobilized chromogens, resulting in color development along all or part of the length of the strip. Although many chromogens oxidizable by hydrogen peroxide are known, the two biggest problems observed in using these known chromogens in such a system was that : (1) the oxidation reaction rate of the chromogens was too slow and (2) the disappearing or fading of color developed in as short as one minute after the plasma migrated past a certain zone. Chromogens which exhibited these problems included o-dianisidine, TMB, 4-chloronaphthol, 3-methyl-2-benzothiazolinone hydrazone (MBTH) plus dimethylaminobenzoic acid (DMAB), 4-methyl-naphthol, and 4-aminoantipyrine plus primaquine.

Many test strips depend upon a colored indicator dye bound to a supporting matrix, generally by covalent bonding. More particularly, the colored dye compound is formed by the coupling of a first and second component of a two component dyes system, the second component of which is covalently immobilized on the matrix. The addition of the first dye component forms a colored covalent adduct covalently immobilized to the matrix.

Nevertheless, colored dye compounds used in analytical test devices have been bound mostly unsatisfactorily to date. Typically, a colored compound is immobilized on the basis of its insolubility relative to the assay solution, which causes it to precipitate onto the matrix without covalent bonding. In other systems, generated color is absorbed, imbibed, impregnated or coated onto the supporting matrix. Patents exemplifying this approach include U.S. Pat. No. 4,069,016; U.S. Pat. No. 4,548,905; U.S. Pat. No. 4,038,031. Limited success at immobilizing color has been achieved by generating localized, precipitated color only at the surface of the solid phase through a signal generating enzyme system immobilized to the support, as disclosed in U.S. Pat. No. 4,435,504.

A number of methods of binding dyes to a matrix are well known in the art. The textile industry binds dye to textiles using mordants which, acting alone or in conjunction with a dye, become absorbed or adsorbed or otherwise intercalated and become stuck on the surface or on the fibers of the textile. Because the mordants and dyes are not covalently bound to the textile, they tend to leach out with washing or other contact with liquids, causing fading and discoloration.

Other known methods for immobilizing dye compounds include providing a dye molecule with a higher alkyl hydrophobic side chain which inserts itself into a hydrophobic substrate or support and is immobilized by hydrophilic/hydrophobic interactions, as disclosed in Bloom et al., U.S. Pat. No. 3,443,939.

Siegel et al., in European patent No. 345 460 disclose a method for covalently immobilizing colored dyes by bonding a second component of a two component dye system to a matrix. The color is formed when the first component, which may be the analyte or another dye component, covalently couples to the second component. The color formed is covalently immobilized to the matrix.

Allen et al., in U.S. Pat. No. 4,999,287, disclose a dye composition for use in a test strip comprising modified N,N-dimethylaniline, i.e., N-(omega-1,2-ethylenediamine carboxamidebutyl), N-methylaniline. This compound is coupled to a paper substrate using carbonyl diimidazole. The paper is activated by soaking the paper in 0.20 M carbonyldiimidazole in methylene chloride, followed by soaking the paper in 1.5 mg/ml of DMA derivative in methylene chloride. Following the covalent attachment of the dimethylaniline analog, the paper is soaked in a 0.5 mg/ml solution of 3-methyl-2-benzothiazolinone hydrazone (MBTH).

Cameron et al., in U.S. Pat. No. 4,394,444, disclose a test device for determination of an analyte in liquid sample comprises an analyte-responsive component comprising a pyridine nucleotide susceptible of reduction in response to the presence of said analyte, and at least one constituent interreactive with the analyte to cause reduction of the pyridine nucleotide, an uncoupler effective to generate an oxidizing substance from the reduced form of the pyridine nucleotide, a peroxidatively active substance, and an indicator which, when oxidized, is not susceptible to reduction by said reduced pyridine nucleotide. The analyte composition disclosed by Cameron et al. is generally used by adding it to a specimen such as urine, cerebrospinal fluid, tissue culture supernatant serum, plasma or whole blood. Test devices can be made by incorporating a carrier with the composition by impregnation, printing or spraying the test composition onto the carrier.

Seitz et al., in *Anal. Chem.* 61: 202–205, 1989, disclose the use of poly vinylalcohol as a substrate for indicator immobilization for fiber-optic chemical sensors. Glutaraldehyde and hydrochloric acid are added to a 5% (w/w) aqueous poly vinylalcohol solution. The resulting gel is clear and transparent in the visible and ultraviolet regions down to about 230 nm. Cyanuric chloride is used to couple indicator to poly vinylalcohol which is then cross-linked with glutaraldehyde. The indicator is covalently bonded to the poly (vinylalcohol) prior to the crosslinking step. Dye fixation is very low (nanograms of dye per gram of poly(vinylalcohol)).

Brenner et al., U.S. Pat. No. 4,035,146, teach a standard method for bonding a compound to a substrate via the use of cyanuric chloride as a linking moiety. However, this method is merely for bonding an antimicrobial compound to a hydroxyl bearing cellulosic substrate such as bandages, clothing, undergarments and bedding, as well as leather or starch.

SUMMARY OF THE INVENTION

It is an object of the present invention to overcome the aforementioned deficiencies. More particularly, the object of the invention is to bond a dye covalently to a polymeric film, especially a polyhydric polymer, for assays and other purposes. The dye may be one which, when it comes into contact with hydrogen peroxide, changes color to indicate the presence of hydrogen peroxide. This dyed film may be used in qualitative or quantitative assays.

The present invention provides a method for chemically immobilizing dyes, indicators, proteins, enzymes, and other molecules in support matrices with much higher yields of immobilized component than are normally found in diagnostic devices.

The covalently immobilized dye of the present invention may be immobilized on solid matrix particles and combined with a free-flowing dye component to form a two component dye system. By combining a dyed film-former with a film-opener, the amount of dye available for assay is greatly enhanced.

The present invention provides a dye system which can be used to detect and measure quantitatively, accurately and precisely high levels of hydrogen peroxide. These high levels of hydrogen peroxide may result from the enzyme-mediated decomposition of various analytes from undiluted whole blood samples.

According to the present invention, both a dyed film-forming polymer and dyed film-opening particles are used in combination to provide a reagent film that reliably changes color, indicating the presence of hydrogen peroxide. This method can also be used for immobilizing high molecular weight molecules such as proteins or enzymes on support matrices.

Of particular interest in the present invention is the two component dye system wherein the first dye component is free flowing and the second component is immobilized to solid matrix particles. The preferred first dye component is MBTH, 3methyl-2-benzothiazolinone-hydrazone, CAS #14448-67-0. The preferred second component is primaquine, [8-(4-amino-1-methylbutylamino)-6-methoxyquinoline]diphosphate salt, CAS #63-45-6. This preferred dye system provides an extended dynamic range for analytes and fast reaction rates. The second component is easily covalently bonded to the matrix according to the process of the present invention. Furthermore, the non-fading characteristics of the current dye system also make it suitable for reactions that involve an oxidase reaction.

The primaquine is covalently attached to two different polyhydric polymers. The MBTH is incorporated into a film which, when the film comes into contact with hydrogen peroxide and peroxidase, changes color to indicate the presence of hydrogen peroxide.

DETAILED DESCRIPTION OF THE PREFERRED EMBODIMENTS OF THE INVENTION

The Matrix

The matrix of the present invention preferably comprises a combination of a film-former and a film opener. These terms are fully defined in Vogel et al., U.S. Pat. No. 4,312,834, the entire contents of which are hereby incorporated by reference.

Many large molecules, such as enzymes, do not penetrate at all, or only penetrate to a small extent into films conventionally used as substrates for assay devices. Because these analytes which are large molecules do not penetrate the films enough to cause a measurable reaction, it has heretofore been difficult to assay accurately a number of large molecules quantitatively. By using a film substrate composed of a film former and a film opener, the large molecules readily penetrate the film substrate, and accurate tests can be devised for large analytes such as hemoglobin, cholesterol, lipoproteins, and enzymes.

A film former is a material that can be used to form a matrix which carries dyes, indicators, and the like in a film. A film opener comprises small insoluble particles which impregnate the film former matrix. The film opener particles in the matrix produce a matrix which is capable of being penetrated by large molecules such as cholesterol, lipoproteins, hemoglobin, and enzymes.

Absorbent, ("open") films are obtained when solid materials in the form of fine, insoluble organic or inorganic particles ("film-openers") are added to dispersions or solutions of film-forming substances from which water-insoluble films are to be formed. The matrices of the present invention thus preferably comprise a water-resistant film containing a film opener in the form of fine, insoluble inorganic or organic particles and the reagents necessary for detection of the desired analyte. Both the film and the film opener carry dye molecules, either the same or different molecules. The film openers of the present invention comprise solid particles which do not take place in the reactions of the assay device. Since these solid particles do not themselves "react", their composition is not critical, and they can comprise, for example, particles of cellulose, kieselguhr, silica gel, precipitated gypsum, calcium carbonate, kaolin, a polyamide, glass, or the like.

The matrix of the present invention preferably comprises two different polymers. Of particular importance is a combination of a film-forming (preferably polyhydric) polymer such as poly vinylalcohol, and a film-opening component, such as cellulose. The two components are fashioned together into a film containing other components that, when they are contacted by hydrogen peroxide, change color to indicate the presence and/or amount of hydrogen peroxide.

As described by Vogel et al., supra, the combination of film-former and film opener has been found to be far superior to paper films in quantitative measurements of components of fluids. The films comprise a water-resistant film containing a film opener in the form of fine, insoluble inorganic or organic particles along with the reagents necessary for detection of the components of the fluid sample.

The matrices of the present invention are prepared by combining a film former comprising a water-resistant film and a film opener in the form of fine, insoluble inorganic or organic particles and the reagents necessary for the detection of the analyte of interest covalently coupled to the matrix. Since the solid film opener does not itself enter into the reaction for the assay, the composition of the film opener is not critical.

Of particular importance for the present invention is the fact that both the film-former and the film opener are dyed. This greatly increases the amount of dye available for providing a visible indicator of the reaction. To prepare this greatly improved matrix, a solution of a dyed film-former is prepared, and a dyed film opener is added thereto. This mixture is then cast into films which have a great amount of dye available for use in an assay.

Dispersions or solutions of a mixture of the the film-forming materials can be coated onto a substrate to give a uniform layer which, after drying, gives a water-resistant film. The film can be used with a substrate as a carrier or, for carrying out a detection reaction, can be pulled off of the substrate and/or applied to another carrier. Carriers for the coated films are preferably synthetic resin films, although other films and foils, papers, fabrics, synthetic resin plates, glass, metal and the like can also be used as carriers if it is appropriate for the purpose of use. Although polyester fabric is the preferred support onto which the film is cast, because the fabric affects only the flow of the device and not the chemistry of the reaction, any suitable support material can be used within the purview of the present invention.

The ratio of the solid material, or film opener, to the film former can range from about 20:1 to about 0.5:1, and is preferably about 5:1 to about 1:1. The ratio depends upon the nature of the film opener and the film former used, as well as upon the intended use. With increasing amounts of film opener and increasing specific surface are of the material employed, the film becomes more absorbent.

When the diagnostic agent according to the present invention is to be used for the detection of high molecular weight and corpuscular materials, the ratio of film opener to film former is preferably 1:1 to 20:1, and more preferably 2:1 to 5:1; when it is to be used for the detection of low or medium molecular weight substances the ratio of film opener to film former is preferably 0.5:1 to 2:1.

If the proportion of film opener exceeds a certain limit, then the film becomes mechanically unstable. If too little film opener is added to the film, then it is impermeable to high molecular weight and cellular components. Thus, for example, the ratio of film opener to film former is preferably 5:1 to 2:1 when polyamide or precipitated gypsum is used as the film opener and an aqueous dispersion of poly vinyl propionate is used as the film former. If, on the other hand, kieselguhr is used, then the ratio should preferably be 2:1 to 1:2. For a particular choice of film opener and film former, the permeability and stability limits on the ratio are readily determined by routine experimentation.

Preferred film formers include organic synthetic resins, such as polyvinyl esters, polyvinyl acetals, polyacrylic esters, poly methacrylic acid, polyacrylamides, polyamides, polystyrene and copolymers of, for example, butadiene and styrene and of maleic acid esters and vinyl acetate. However, other film-forming materials including, natural and synthetic organic polymers,as well as mixtures thereof, can be used, preferably in the form of aqueous dispersions. Alternatively the film formers can also be dissolved in organic solvents, such as a copolymer of vinyl chloride and vinyl propionate dissolved in ethyl acetate. Other polymeric film-forming substances which can be used in the present invention include polyvinyl acetate, gelatin, poly vinylpyrrolidone, poly vinylpropionate, and the like for binding dyed particles such as cellulose or silica. Polyhydric polymers are especially preferred because they are readily dyed with MBTH/ primaquine, as discussed more fully in the next section.

Other polymers that can be used for the film-former in the method of the present invention include polystyrene, poly vinylacetate, poly methylmethacrylate, and the like. Since none of these polymers is polyhydric in nature, none of these polymers can be readily dyed with the same reactive dye system as is used for poly vinylalcohol, since none of the above polymers has the appropriate sites for dye fixation. However, other dye molecules can be used which can attach to the sites for dye fixation onto the polymers. One skilled in the art can readily determine without undue experimentation which dyes can effectively be coupled to each film forming material. MBTH, which was added as the hydrochloride salt in the poly vinylalcohol system, can be used equally well in its free-base form, which is soluble in a variety of organic solvents that dissolve the film-forming polymers in these alternate systems, such as dichloromethane, toluene, chloroform, benzene, acetone, methanol, and the like.

Preferred film openers are substantially chemically inert particulate materials. Particulate materials that can be used as a film opener in the present invention include microcrystalline cellulose, kieselguhr, precipitated gypsum, calcium carbonate, kaolin, a polyamide, or the like. Alternative film opening materials include cellulose powder, cellulose pulp, paper and cotton fabrics of many types. Supports which can be used in the process of the present invention include silica, glass, alumina, latex and the like.

The dyed film former is mixed with the dyed film opener in either solution or dispersion and applied to a substrate to give a thin film, and the liquid is evaporated. The resultant film is then ready for use in a clinical assay.

In one embodiment of the present invention, the same dye component( i.e., primaquine) is used to dye both film-former and film-opener.

The Dye Component

A covalent bond between a dye molecule and a matrix can only be established if the matrix to which the dye is to be bound contains suitable groups which can be substituted. These groups must not only be present in sufficient quantity to enable thorough dying, but the groups must also react under conditions which can be realized in the process. Among the suitable groups are hydroxyl, thiol and amino, although other suitable groups may be used depending upon the dye which is to be bound to the matrix. One skilled in the art of organic synthesis can readily determine what matrices are suitable for this purpose, depending upon the particular dye used.

Hydroxyl, thiol and amino are present mainly in cellulosic and protein fibers, which are formed from natural polymers. Synthetic polymers which contain hydroxyl groups, such as poly vinyl alcohol are likely reaction partners for reactive dyes, which means that reactive dyes can react in an alkaline medium with a wide variety of aliphatic hydroxy compounds.

Among the most commonly used reactive dyes for hydroxylcontaining compounds are dyes containing the dichlorotriazinyl group or the monochlorotriazinyl group. Among the dyes that have been used in this fashion are dyes containing the following groups:

monochlorotriazinyl dichlorotriazinyl 2,4-dichloropyrimidinyl 2,4,5-trichloropyrimidinyl 2,3-dichloroquinoxaline-6-carbonyl 4,5-dichloro-6-pyridazonylpropionyl 1,4-dichlorophthalazine-6-carbonyl chlorobenzothiazole linked to the dye molecule via —CONH—, $SO_2NH$—, —NH—, or N=N—

5-chloro-4-methyl-2-methylsulfonylpyrimidinyl vinylsulfonyl

β-sulfatoethylsulfonyl

β-sulfatoethylaminosulfonyl

β-chloroethylsulfonyl

β-sulfatopropionamido

Most of these groups react by nucleophilic substitution.

The preferred dye component of the present invention is a combination of primaquine and MBTH. It was found that this dye combination formed a red oxidized chromogen complex which was resistant to the undesirable reduction by other agents in plasma sample, as was observed with many other chromogens tried. Furthermore, when the concentration of the substrate in the sample was high enough to cause oxygen depletion, other chromogens suffered reduction and loss in color by the action of oxidase while the preferred chromogen system of the present invention did not.

In order to ensure that the dyes are covalently coupled to the film both the polymeric film-former and the film opener are preferably activated with an activating compound such as cyanuric chloride. The dye component, such as primaquine, is added thereto until the dye has coupled to the support materials. The high dye yield procedure for the present invention further includes treating the film opener with sodium hydroxide prior to cyanuric chloride activation.

The polyvinyl alcohol may be dyed according to the same high-dye-yield procedure used for cellulose. However, because the polyvinyl alcohol treated with cyanuric chloride is so highly substituted, it no longer is soluble, even in highly polar solvents such as DMSO, rendering it useless as a film-forming polymer. In comparison, unmodified poly vinylalcohol, of molecular weight about 50,000, dissolves readily in hot water, up to about 40% solids. For paste formulations, the low-dye-yield untreated polyvinylalcohol was generally used.

Poly vinylalcohol may be dyed using a linking moiety other than cyanuric chloride. Alternative linking moieties which can be used in the process of the present invention include carbonyldiimidazole, ethyl-N,N-dimethylpropyl carbodiimide, and the like, which are useful for the immobilization of the dye.

Of the dye compositions that can be used in the process according to the present invention, the combination of MBTH with primaquine was found to be the most advantageous. The color development time with this dye pair was very short, and the end product color was stable and very intense.

In a preferred embodiment of the present invention, the matrix material, such as cellulose or polyvinyl alcohol, is pretreated by contacting the cellulose or polyvinyl alcohol with an aqueous solution of a strong base such as sodium or potassium hydroxide prior to activation.

The method of the present invention thus has provided a way to maximize the amount of reactive material covalently bound to the film-opener as well as the film former. In an especially preferred embodiment, large amounts of dyes are fixed onto an activated film-opener, such as cellulose dichlorocyanurate, first by stirring the cellulose dichlorocyanurate in a hot (60°–75° C.) dye bath containing the dye and a suitable salt such as sodium chloride. The support is stirred in the hot, aqueous high ionic-strength bath for up to about 30 minutes, after which the dye is fixed through the action of a fixing reagent such as sodium carbonate or sodium hydroxide.

The present invention is further illustrated, but not limited, by the following examples.

EXAMPLE 1

Primaquine-Dyed Poly Vinylalcohol

Poly vinylalcohol was first washed of lingering acid from its preparation by stirring 60 grams of poly vinylalcohol, molecular weight about 50,000, in 250 mL 1:1 (v/v) water/acetone. This mixture was stirred for fifteen minutes. The mixture was collected in a Buchner funnel, removed, spread in a glass pan, and dried at 5% relative humidity (R.H.) overnight.

The poly vinylalcohol was activated with cyanuric chloride (s-trichlorotriazine) by dissolving 25 grams of cyanuric chloride in about 400 mL acetone in a one-liter Erlenmeyer flask. The mixture was stirred for about two minutes to dissolve the cyanuric chloride, and 50 grams of poly vinylalcohol from above were added with 200 mL water. This mixture was stirred for about 15 hours, and it was noted that heat was evolved. The product was collected in a Buchner funnel and was rinsed with 400 mL of a 1:1 mixture of acetone and water. The product was spread in a glass pan and dried at 5% relative humidity (R.H.) for up to three hours.

Free-base primaquine was made by dissolving 6 grams primaquine diphosphate in 150 mL water. One hundred mL of an aqueous 15% sodium hydroxide solution were prepared, and all of the sodium hydroxide solution was added to the primaquine solution. The free-base primaquine precipitated out of solution. The contents of the flask were poured into a 500-mL separatory funnel, and the aqueous solution was extracted with 300 mL ether in four 75 mL portions. All of the ether extracts were combined, and were extracted with 100 mL water, then with 100 mL brine. The ether solution was dried over granular anhydrous sodium sulfate. The ether solution was evaporated under reduced pressure. The free-base primaquine obtained was a viscous yellow syrup.

To dye the activated poly vinylalcohol, the dried activated poly vinylalcohol and 400 mL acetone were combined in an Erlenmeyer flask. The free-base primaquine was dissolved in several mL acetone and added to the activated poly vinylalcohol solution. The flask was stoppered, shrouded in foil, and left to stir overnight, about 20 hours. The product was collected in a Buchner funnel.

The dyed poly vinylalcohol was then washed of lingering free dye by washing the product in about 500 mL acetone, while stirring for about ten minutes. The product was collected in a Buchner funnel. The product was washed with about 500 mL water with stirring for about ten minutes. This product was collected in a Buchner funnel. A small sample of the product was placed into a test tube and covered with 2 mL water and shaken. This was then centrifuged at 3000 rpm for about one minute. Then, 0.5 mL of supernatant was siphoned off and placed into another test tube. This was developed with three drops of 2 mM MBTH, 3 drops of 1.2 mg/mL peroxidase solution and three drops of 20 mM hydrogen peroxide. If the sample turned pink, the product was washed again with water, then acetone, and the test repeated. Washing was continued until the test was negative, as evidenced by the formation of a yellow (rather than red) color. The material was dried in a dry-room and stored at room temperature.

EXAMPLE 2

Primaquine-Dyed Cellulose

Cellulose was pretreated with sodium hydroxide by combining 20 grams microcrystalline cellulose (either FMC Avicel PH-105 or Lattice NT-006) with 200 mL 15% aqueous sodium hydroxide solution in a beaker, and stirring at room temperature for about 20 minutes. The sodium cellulose was collected in a Buchner funnel, but the product was not rinsed. The caustic-soaked material was transferred to a beaker with a rubber spatula.

To activate the sodium cellulose with cyanuric chloride, 20 grams of cyanuric chloride were dissolved in 400 mL 1:1 toluene/dioxane (v/v). This solution was added to the beaker containing sodium cellulose. The mixture was stirred mechanically for 30 minutes. making sure that the wet cellulose was well dispersed in the organic solvent. The product was collected in a Buchner funnel.

The activated cellulose was washed scrupulously by transferring the cellulose dichlorocyanurate back to the beaker, and washing it by stirring mechanically for ten minutes each according to the following regimen:

twice with 400 mL dioxane once with a solution of water, 200 mL, 20 mL glacial acetic acid, and 180 mL dioxane once with 400 mL water twice with 400 mL acetone The washed cellulose dichlorocyanurate was sieved and was dried at 5% R.H. for at least two hours.

To dye the cellulose dichlorocyanurate, the cellulose dichlorocyanurate was combined in a beaker with 6 grams primaquine diphosphate, 200 mL water and 8 grams sodium chloride. The mixture was warmed on a stirring hot plate to 60°–65° C. The dye was fixed by adding anhydrous sodium carbonate by the spoonful, noting the release of carbon dioxide, until the dye liquid attained a pH of 10 by litmus. The mixture was stirred an additional ten minutes, and the product was collected in a Buchner funnel.

The dyed cellulose was washed four times in 400 mL acetone, once with 400 mL water, and then with 400 mL acetone.

The unreacted sites on the dyed cellulose were then capped with 1% bovine serum albumin or glycine solution. The washed cellulose was added to either the bovine serum albumin or glycine solution (5 grams bovine serum albumen or 5 grams glycine, 500 mL water) and stirred at room temperature for 1.5 hours. The dyed cellulose was collected, washed with water, then acetone. The product was stirred in acetone, collected, and dried.

EXAMPLE 3

Preparation of a Reagent Paste in Aqueous Solution

Three grams of primaquine-dyed microcrystalline cellulose were dispersed in 30 mL 0.1 M sodium phosphate monobasic buffer, pH 4.2, and then centrifuged. Supernatant buffer solution was decanted off and the buffer-saturated cellulose was transferred to a beaker. Four grams of primaquine-dyed poly vinylalcohol were combined with 6.0 grams of the same phosphate buffer solution. The slurry was briefly microwaved until the poly vinylalcohol solution dissolved, about 15 seconds on high power. The poly vinylalcohol solution was added to the buffer-saturated cellulose, and the mixture was stirred mechanically for several minutes to give a uniform paste. The paste was fully cooled to room temperature.

Then 1.5 mL of a 40 mg/mL aqueous solution of MBTH and 9.2 mg of horseradish peroxidase (Toyobo, type PE0310, reconstituted in 0.5 mL water) were added to the cooled paste, and the entire formulation was stirred to ensure complete mixing.

EXAMPLE 4

Preparing a Reagent Paste in Non-Aqueous Solvent

Primaquine-dyed microcrystalline cellulose, 3.7 grams, was dispersed in 30 mL absolute methanol, and then centrifuged. Supernatant was decanted off and the methanol-saturated cellulose was transferred to a beaker. Next, 1.3 gram of a 40% methanolic poly vinylacetate solution was added to the dyed cellulose. This mixture was stirred mechanically for several minutes to give a uniform paste. MBTH (1.0 mL of a 40 mg/mL methanolic solution of the hydrochloride salt) and 8.8 mg of horseradish peroxidase (Toyobo, type PEO310, reconstituted in 0.5 mL water) were added to the cooled paste, and the entire formulation was stirred to ensure complete mixing. The aqueous enzyme solution can be added without precipitating the dyed poly vinylalcohol, provided the amount of water used is very small.

EXAMPLE 5

Casting a Reagent Film from Paste

A 12"×5" swatch of polyester fabric (PeCap® from Tetko, Briarcliffe Manor, N.Y.) was attached to a glass plate using double-stick tape. A paste such as described in Example 3 or Example 4 was placed at one end of the swatch, and a film was drawn down onto the fabric using a film-casting knife (Paul N. Gardner Company, Pompano Beach, Fla.) set at 5 mils (0.005 inch). The film was dried quickly in a low-humidity atmosphere (5% or less relative humidity) for four hours until fully dry.

EXAMPLE 6

Performance of Dyed Film

A paste was made as in Example 4 and cast into a film as in Example 5.

A 10mm × 100 mm strip of the dried film (reagent layer) was combined with a slightly longer strip of polyester fabric which had been treated with poly vinylalcohol and dried (wicking layer). These two strips were heat-sealed onto a non-porous plastic backing material such that the wicking layer was positioned between the reagent film and the non-porous backing. The channel in the heat-sealed device was 3 mm wide × 92 mm long.

A solution of hydrogen peroxide (5 mM, 50 µL) was spotted onto the wicking layer at one end of the reagent layer and allowed to wick up the entire length of the channel, creating a colored bar the entire width of the channel and 37 mm in length. The color in the remainder of the channel remained unchanged. The colored bar ended at the point there where the hydrogen peroxide was entirely consumed by the action of the various components of the reagent layer, namely, primaquine, MBTH and peroxidase, causing the desired change in color in relation to the amount of hydrogen peroxide present. The end of the run was determined by observing solution emerge from the opposite end of the channel on the reagent layer.

To prepare the reagent pastes, the preferred formulation was low-dye-yield poly vinylalcohol dissolved in hot water as a film-former, and high-dye-yield 6-micron FMC Lattice NT-006 microcrystalline cellulose as the film opener.

The immobilized dye system of the present invention is particularly well suited for use in assay devices such as those disclosed in Ertingshausen, U.S. Pat. No. 5,087,556 and Ertingshausen, Ser. No. 07/749,521, filed Aug. 26, 1991 now U.S. Pat. No. 5,234,813.

Basically, these assay devices comprise a first open reservoir, a channel in which is incorporated a diagnostic agent and indicator means, and a second open reservoir. The dye system of the present invention is placed into the channel and functions well as an indicator.

COMPARATIVE EXAMPLES

"Microscopic" cellulose (particulate, such as powdered cellulose or microcrystalline cellulose) rather than "macroscopic" cellulose in the form of paper, was dyed by first activating the cellulose with cyanuric chloride, and then treating the activated cellulose with a reactive dye such as primaquine. The increased surface area in the finely divided cellulose improved the dye density over the macroscopic cellulose.

Dyed cellulose particles as prepared above were mixed with polymeric carriers such as cellulose acetate, modified cellulosics such as Aqualon®, carboxymethylcellulose, Natrosol, Klucel and the like, for subsequent application to a wicking material such as paper, absorbent membranes, fabric or the like. These combinations were not successful because the particle distribution in the preparations was poor, the hydrophilicity and flow were often poor, and the color change was often erratic.

However, it was found that adding the dyed cellulosic particles as prepared above with a solution of a film forming material, such as polyvinyl alcohol, yielded very high functionalization of the dye carrier matrix (from a homogeneous rather than a heterogeneous mixture), but also eliminated the problem of poor dye-particle distribution of a carrier.

Comparison of Prior Dyed Film Former

A paste was prepared, essentially according to the method of Vogel et al., in U.S. Pat. No. 4,312,834, to provide a substrate comprising both a film opener and a film former. A dispersion was prepared with the following composition:

| | |
|---|---|
| cellulose | 5 g |
| polyvinyl propionate dispersion (50% in water) | 3 g |
| methylhydroxypropyl cellulose | 0.042 g |
| titanium dioxide powder | 2 g |
| cholesterol esterase | 1,200 U |
| cholesterol oxidase | 800 U |
| peroxidase | 26,000 U |
| a solution of 0.2 g 3,3',5,5'-tetramethylbenzidine and 0.17 g dioctyl sodium sulfosuccinate in | |
| 0.74 ml acetone | 1 mL |
| potassium dihydrogen phosphate | 0.049 g |
| disodium hydrogen phosphate dihydrate | 0.167 g |
| distilled water | 19.5 ml |

The above mixture was applied to a polycarbonate film in a 300 µ thick layer and subsequently dried with warm air.

When a solution of hydrogen peroxide was applied to the matrix so formed, a color change was observed. Unfortunately, there was insufficient dye for the required dynamic range of many clinically useful assays, particularly when using undiluted blood samples.

Dyed matrices were prepared according to several previously known methods and compared with a matrix dyed according to the method of the present invention. The relative dye densities of the dyed matrices were compared.

A. Periodate Oxidation

Filter paper was oxidized with periodate and dyed with primaquine according to the method of European patent 0 345 460. Ten grams of Schleicher and Schuell grade 410 paper was added to a solution of 10 g of sodium periodate in 200 mL of distilled water at room temperature, and the paper and solution were agitated on a rotary shaker for three hours. Thereafter, the periodate solution was poured off and 200 mL of distilled water was added. After 15 minutes, the water was poured off and another 200 mL of fresh distilled water was added. This last step was repeated two additional times to produce an activated paper ready for coupling. The periodate activated paper was added to a vessel containing 100 ml of 0.1 M sodium phosphate buffer pH 7.4 and 0.5 g of primaquine. The solution and paper were agitated overnight at room temperature on a rotary shaker. After incubation, the solution was poured off of the dye coupled paper, and the dyed paper was rinsed once with 200 mL of distilled water. The paper was then washed with 200 mL of fresh distilled water every 30 minutes until the concentration of the dye in the water fell below 5 µg per mL. The sheets were allowed to air dry prior to use.

Even after the dying step with prior periodate oxidation, the dye density on the paper was insufficient for the required dynamic range of the device, i.e., 150–300 mg/dL cholesterol in undiluted plasma samples.

B. Carbonyl Diimidazole Activation

This method is the activation method disclosed in Allen et al., U.S. Pat. No. 4,999,287. Strips of Whatman 31ET chromatography paper were first activated by soaking in 0.20 M carbonyldiimidazole in methylene chloride. This activated paper was then soaked in 1.5 moles of a modified N,N-dimethylaniline, N-[Ω-1,2-ethylenediamine carboxamido-butyl], N-methylaniline in methylene chloride. Following the covalent attachment of the dimethylaniline analog, the paper was soaked in a 0.5 mg/mL solution of 3-methyl-2-benzothiazolinione hydrazone (MBTH). Excess solution was wiped off gently by wiping the paper over one edge of a dish, followed by drying the paper in a forced air convection oven at 50° C. for about 25 minutes.

C. Cyanuric Chloride Activation

Poly vinylalcohol and dyed microcrystalline cellulose were prepared by the method of Seitz and Sundberg, *Anal. Chem.* 61: 02–205, 1989. This method was as follows:

Cyanuric chloride (0.5 g) was dissolved in 20.0 mL of acetone, and 1.0 gram of poly vinylalcohol and 10.0 mL of water were added. The mixture was stirred and allowed to react for 20 minutes at room temperature. The poly vinylalcohol was insoluble in this medium, and was separated by filtration. After the poly vinylalchol-cyanuric chloride conjugate formed, it was washed with 50 mL of 1:1 acetone:water. The conjugate was then reacted with 10.0 mL of a solution containing 10 mg primaquine in acetone. After 30 minutes at room temperature, the product was separated and washed, first with acetone and then with water until no further unreacted indicator could be observed in the washings. The material was then dried and stored as a solid.

Cyanuric chloride (0.5 g) was dissolved in 20.0 mL of acetone, and 1.0 gram of microcrystalline cellulose and 10.0 mL of water were added. The mixture was stirred and allowed to react for 20 minutes at room temperature. The microcrystalline cellulose was separated by filtration. After the microcrystalline cellulose-cyanuric chloride conjugate was washed with 50 mL of 1:1 acetone:water, the conjugate was reacted with a 10.0 mL solution containing 100 mg primaquine in acetone. After 30 minutes at room temperature, the product was separated and washed, first with acetone and then with water until no further unreacted indicator could be observed in the washings. The material was then dried and stored as a solid.

Both the poly vinylalcohol and the microcrystalline cellulose dyed in this matter remained colorless after the attachment of the dye. Both materials developed a pink color upon exposure to hydrogen peroxide in the presence of MBTH and peroxidase.

Unfortunately, the dye density in films prepared as above was insufficient for the required dynamic range of the device for may clinical assays. It should be noted that the Seitz and Sundberg method was developed primarily for chromatographic applications and other similar technologies, using other linking groups such as carbonyldiimidazole, ethyl-N, N-dimethylpropylcarbodiimide, etc., developed for immobilization of antibodies, proteins, enzymes and the like, this method was insufficient to provide test strips for use in most clinical assays.

D. Present Method

A reagent paste was prepared as described in Example 3 of the present application and was cast onto a swatch of polyester as described in Example 5.

Results

The dye density on cellulose using the method of the present invention, D, was compared with the dye density on cellulose as treated by methods A, B and C, above. It can readily be seen from Table 1 that the method of the present invention provide a method for dye immobilization that results in a much higher yield of dye as compared with that obtained by conventional methods.

TABLE 1

| IMMOBILIZATION METHOD | RELATIVE DYE DENSITY |
|---|---|
| A. PERIODATE | 1.82 |
| B. CARBONYL DIIMIDAZOLE | 1.00 |
| C. CYANURIC CHLORIDE | 1.12 |
| D. PRESENT INVENTION | 5.24 |

In order to compare the matrices prepared for dye density, each matrix was subjected to reflectance spectroscopy over the full spectrum to obtain a relative dye density. For convenience in comparing the relative dye densities, the dye density obtained by carbonyl diimidazole activation, method B, which had the lowest dye density of the four matrices, was chosen as the standard and assigned a relative density of 1.00. Of course, any one of these matrices could have been assigned a relative density of 1.00 and the remaining dye densities compared to that matrix.

It was found that relative dye densities in excess of about 2.50 times the dye density obtained by carbonyl diimidazole activation as described in B above, can successfully be used for strip assay devices for a wide range of assays. The method of the present invention thus provides a dyed matrix for use in clinical assays that is sensitive enough to detect and quantify a great many analytes.

Color Formation

Table 2 illustrates the rapid reaction rate of chromogen systems when prepared according to the present inventions, in that the ultimate absorbance was reached within the first minute. This absorbance did not change substantially over a period of thirty minutes.

TABLE 2

| CHROMOGEN SYSTEM | WAVELENGTH | ABS (1 min) | ABS (30 min) |
|---|---|---|---|
| 1. Primaquine/MBth | 514 nm | 0.394 | 0.394 |
| 2. 4 - AAP/Phenol | 514 nm | 0.317 | 0.363 |
| 3. 4 - AAP/Primaquine | 576 nm | 0.515 | 0.271 |
| 4. TMB | 470 nm | 0.454 | 0.116 |

TABLE 2-continued

| CHROMOGEN SYSTEM | WAVELENGTH | ABS (1 min) | ABS (30 min) |
|---|---|---|---|
| 5. 4 - AAP/4-Cl-phenol | 514 nm | 0.451 | 0.522 |
| 6. 4 - chloronapthol | 514 nm | 0.490 | 0.600 |

Using undiluted plasma samples the assay for glucose conducted with the above chromogens usually has a dynamic range of from 20 to about 250 mg/dL. The chromogen composition of the present invention gave twice that analytical range. Additives to extend the dynamic range, such as pyrogallol, as described in U.S. Pat. No. 4,971,918, are therefore not necessary.

The chromogen system based upon MBTH/primaquine was one of the fastest reacting pairs found. Table 3 shows rates of color bar formation for peroxide reagent film using primaquine/MBTH dye system: 3.4 grams primaquine immobilized on cellulose, 20 mg MBTH, 1.1 gram polyvinyl acetate (40% in methanol) and 9 mg peroxidase.

TABLE 3

| Peroxide Concentration | Color Bar (cm) |
|---|---|
| 5 mM | 4.7 |
| 8 mM | 8.0 |

The chromogen combination of the present invention has a second component that contains a primary amine group that is not involved in the chromogen complex, thus permitting the use of straightforward immobilization procedures.

The chromogen system of the present invention can be used in solid phase reagent strips employing oxidases and generating hydrogen peroxide. The second component of the chromogen is immobilized onto a solid matrix such as cellulose, silica, latex beads, or the like. The first component is absorbed onto the support surface.

The detection system of the present invention can be used particularly to detect the presence and amount of hydrogen peroxide generated by a reaction with an analyte in a fluid sample. Among the analytes that can conveniently be tested by generation hydrogen peroxide are cholesterol, uric acid, choline esterase, phospholipids, creatine, or creatinine.

The process and films and dyes of the present invention can be used for preparing static assay devices such as dipsticks. Of particular importance is non-bleeding dipsticks, in which the immobilization of a dyestuff is of great importance.

The foregoing description of the specific embodiments will so fully reveal the general nature of the invention that others can, by applying current knowledge, readily modify and/or adapt for various applications such specific embodiments without departing form the generic concept, and therefore such adaptations and modifications are intended to be comprehend within the meaning and range of equivalents of the disclosed embodiments. It is to be understood that the phraseology or terminology herein is for the purpose of description and not limitation.

All patents, patent applications, and nonpatent publications cited herein are hereby incorporated by reference. No admission is made that any cited reference constitutes prior art.

What is claimed is:

1. A matrix for colorimetrically detecting or quantifying hydrogen peroxide in a sample comprising:

a film-forming component to which is covalently bonded a first dye, and a film-opening component to which is covalently bonded a second dye;

wherein said first dye and said second dye are optionally the same;

said film-opening component comprises small insoluble particles which impregnate the film former matrix and are not reactive with any reagents associated with the film-forming component.

2. The matrix according to claim 1 wherein said film-forming component is selected from the group consisting of polyvinyl alcohol, polystyrene, polyvinyl acetate, polyvinyl esters, polyacrylamides, polyamides, polymethylmethacrylate, and copolymers of butadiene and styrene and copolymers of maleic acid esters and vinyl acetate and mixture thereof.

3. The matrix according to claim 1 wherein said film-opening component is selected from the group consisting of cellulose, microcrystalline cellulose, kieselguhr, silica gel, precipitated gypsum, calcium carbonate, kaolin, polyamides and glass.

4. The matrix according to claim 1 wherein said first dye is primaquine and said second dye is 3-methyl-2-benzothiazolininone-hydrazone.

5. The matrix according to claim 1 wherein a relative dye density in said matrix is at least 2.5 relative to the dye density of a carbonyldiimidazole activated paper substrate dyed with said first dye.

6. A method for immobilizing a dye molecule onto a polymeric film substrate having at least one group selected from the group consisting of hydroxyl, thiol and amino, said dye molecule selected from the group consisting of compounds that can covalently bond to a hydroxyl, thiol or amino group, comprising:

treating said polymeric film substrate with a linking moiety to activate said polymeric film substrate:

covalently bonding said dye molecule onto said activated polymeric film substrate;

combining said dyed polymeric film substrate with a dyed film-opener.

7. The method according to claim 6 wherein said dyed film-opener is mixed with a dyed polymeric substrate in solution.

8. The method according to claim 6 wherein said linking moiety is selected from the group consisting of cyanuric chloride, carbonyldiimidazole, and ethyl-N,N-dimethylpropyl carbodiimide.

9. The method according to claim 6 wherein said polymeric film substrate is selected from the group consisting of cellulose and polyvinyl alcohol.

10. The method according to claim 6 wherein said polymeric film substrate is cellulose and said cellulose is pretreated by contacting said cellulose with an aqueous solution of sodium hydroxide prior to activation.

11. The method according to claim 6 wherein said polymeric film substrate is polyvinyl alcohol and said linking moiety is cyanuric chloride.

12. The method according to claim 6 wherein said dye molecule is a dye containing a group selected from the group consisting of dichlorotriazinyl and monochlorotriazinyl.

13. The method according to claim 11 wherein said dye molecule is primaquine.

14. The method according to claim 6 wherein said dye molecule is selected from the group consisting of monochlorotriazinyl dichlorotriazinyl 2,4-dichloropyrimidinyl 2,4,5-trichloropyrimidinyl 2,3-dichloroquinoxaline-6-carbonyl 4,5-dichloroquinoxaline-6-carbonyl 1,4-dichlorophthalazine-6-carbonyl chlorobenzothiazole linked to the dye molecule via —CONH—, SO$_2$NH—, —NH— or —N=N—

5-chloro-4-methyl-2-methylsulfonylpyrimidinyl vinylsulfonyl

β-sulfatoethylsulfonyl

β-sulfatoehtylaminosulfonyl

β-chloroethylsulfonyl and

β-sulfatopropionamido.

15. The method according to claim 14 wherein said polymeric film substrate contains a hydroxyl group.

16. The method according to claim 6 wherein said polymeric film substrate is selected from the group consisting of polyvinyl alcohol, polystyrene, polyvinyl acetate, polyvinyl esters, polyacrylamides, polyamides, polymethylmethacrylate, polyvinyl acetals, polymethacrylic acid, copolymers of butadiene and styrene, copolymers of maleic acid esters and vinyl acetate, copolymers of vinyl chloride and vinyl propionate, and mixtures thereof.

17. The method according to claim 13 wherein MBTH is added to said dye.

18. The method according to claim 6 wherein said polymeric film substrate is not cellulose, starch or leather.

* * * * *